United States Patent [19]

Schaefer et al.

[11] Patent Number: 6,123,451
[45] Date of Patent: Sep. 26, 2000

[54] PROCESS FOR DETERMINING A TISSUE COMPOSITION CHARACTERISTIC OF AN ANIMAL

[75] Inventors: Allan L. Schaefer; Alan Kwai-Wah Tong, both of Lacombe, Canada

[73] Assignee: Her Majesty the Queen in right of Canada, as represented by the Administer for the Department of Agiculture and Agri-Food (AFCC), Lacomb, Canada

[21] Appl. No.: 09/039,630

[22] Filed: Mar. 16, 1998

Related U.S. Application Data

[60] Provisional application No. 60/039,202, Mar. 17, 1997.
[51] Int. Cl.[7] .......................... G01N 25/00; G01N 33/12; A22B 5/00
[52] U.S. Cl. ................ 374/45; 374/124; 99/493
[58] Field of Search ................ 374/45, 4, 124; 99/493, 485

[56] References Cited

U.S. PATENT DOCUMENTS

| | | | |
|---|---|---|---|
| 3,877,818 | 4/1975 | Button et al. | 356/416 |
| 3,948,249 | 4/1976 | Ambroshini | 600/551 |
| 4,009,390 | 2/1977 | Satterlee et al. | 378/45 |
| 5,017,019 | 5/1991 | Pompei | 374/133 |
| 5,353,796 | 10/1994 | Schroeder et al. | 600/437 |
| 5,458,418 | 10/1995 | Jones et al. | 374/45 |
| 5,474,085 | 12/1995 | Hurnik et al. | 600/587 |
| 5,483,441 | 1/1996 | Scofield | 364/400 |
| 5,595,444 | 1/1997 | Tong et al. | 374/45 |

FOREIGN PATENT DOCUMENTS

| | | |
|---|---|---|
| 2099532 | 1/1995 | Canada . |
| WO 94/00997 | 1/1994 | WIPO . |
| WO 95/01567 | 1/1995 | WIPO . |

OTHER PUBLICATIONS

Scott et al., "What Effect Does Transportation Have on Heat Loss in Cattle?", Lacombe Research Highlights 1991, pp. 20–21.

Gariepy et al., "Early Prediction of PSE and DFD by Infrared Thermography on Live Animals", Proc. Int. Congr. On Meat Science Technology, vol. 2, pp. 403–405 (1987).

Garry B. Desroches, "Stress Affected Livestock as seen by Thermography", Proceedings of the International Society for Optical Engineering, 1988, vol. 934, pp. 120–129.

(List continued on next page.)

*Primary Examiner*—Diego Gutierrez
*Assistant Examiner*—Stanley J. Pruchnic, Jr.
*Attorney, Agent, or Firm*—Finnegan, Henderson, Farabow, Garrett & Dunner, L.L.P.

[57] ABSTRACT

A process for determining a tissue composition characteristic of a live animal or carcass involves the steps of: (a) obtaining either or both of at least one infrared thermographic image of the animal while it is alive, taken from at least one view, or at least one image of the carcass of the animal after slaughter, taken from at least one view, each thermographic image being capable of being represented as an array of pixels providing temperature data representative of temperature information at the corresponding part of the image; (b) calculating the value of at least one statistical measure of the temperature data for each thermographic image; (c) providing a predictive model wherein the tissue composition characteristic is included as an output variable, and the statistical measures of temperature data for each thermographic image are included as input variables; and (d) solving the predictive model to provide the value of the tissue composition characteristic. The process of the invention is useful in a wide variety of homoeotherinic animals. Tissue composition characteristics of interest include, without limitation, lean body mass, grade, carcass yield and rib eye area. An apparatus for performing the processes of the invention includes: (a) image acquisition means for obtaining the infrared thermographic images; (b) computing and storage means for storing each image as an array of pixels, calculating the value of statistical measures of the temperature data for each thermographic image, and providing and solving the predictive model; and (c) output means for providing an output of the value of the tissue composition characteristic.

38 Claims, 1 Drawing Sheet

OTHER PUBLICATIONS

Allan L. Schaeffer, et al., "Infrared Thermography of Pigs with Known Genotypes for Stress Susceptibility in Relation to Pork Quality", Can. J. Anim. Sci., 1989, vol. 69, pp. 491–495. (Jun. '89).

Clark, J.A. and Cena, K. 1973. Thermographic Measurements of the Surface Temperatures of Animals. J. Mammalogy 54:1003–1007.

Dugan, M.E.R., et al. 1997. The effects of porcine somatotropin, gender and porcine stress syndrome on growth, carcass composition and pork quality. Canadian J. Animal Science. 77:233–240.

Forrest, John C. 1995. New Techniques for Estimation of Carcass Composition. In: Quality and Grading of Carcasses in Meat Animals. Edited by S.D.M. Jones. CRC Press N.Y. 7:157–171.

Goll, Darrel E., et al. 1977. Skeletal muscle, nervous system. temperature regulation, and special senses. In: Dukes Physiology of domestic animals. Edited by M.J. Swenson. Comstock Pub. Cornell Univ. Press. Ithaca. 9th ed. 39:504–530.

Hayward, J.A. et al. 1975. Thermal Balance and Survival Time Prediction of Man in Cold Water. Can. J. Physiol. Pharmacol. 53:21–32.

Price, M.A. 1995. Development of Carcass Grading and Classification Systems. In: Quality and Grading of Carcasses in Meat Animals. Edited by S.D.M. Jones. CRC Press N.Y. 8:173–199.

Jones, S.D.M. 1995. Future Directions for Carcass Assessment. In: Quality and Grading of Carcasses in Meat Animals. Edited by S.D.M. Jones. CRC Press N.Y. 10:215–228.

Jones, S.D.M., et al. 1987. The effect of carcass grade and sex on lean content of beef carcasses. Can. J. Anim. Sci. 67:205–208.

Kleiber, Max. 1975. The Fire of Life—an introduction to animal energetics. R.E. Kriefer Publishing Company NY. 10:179–222.

Neilson, N.P. and Clayne R. Jensen. 1972. Measurement and Statistics in Physical Education. Wadsorth Publishing Company, Inc., Belmont, CA. 1:3–5; 2:7–14; 3:15–20; and 8: 93–106.

O'Grady, J.F. 1989. New Techniques in Pig Carcass Evaluation. Editor EAAP Pub. No. 41. Pudoc, Wageningen.

Mitchell, D. 1977. Physical Basis of Thermoregulation. In: Environmental Physiology II. Edited by David Robertshaw. Univ. Park Press, Baltimore. vol. 15, 1:1–27.

SAS Institute Inc. 1985. SAS User's Guide: Statistics, Version 5 Edition. SAS Institute, Inc., Cary, NC. 19:403–432 and 20:433–506.

Steel, R.G.D. and J.H. Torrie. 1960. Principles and Procedures of Statistics. McGraw–Hill Book Company Ltd. NY. 10:183–193 and 14:277–304.

Steel, Robert G.D. and James H. Torrie. 1980. Principles and Procedures of Statistics—A Biometrical Approach. 2 ed. McGraw–Hill Book Company Ltd. NY 2:17–30.

Lamarque, J.L. et al. 1975. Etude Thermographique Experimental en Pathologie Arterielle Peripherique. Ann. Radiol. 18(5):513–523.

PROCESS FOR DETERMINING A TISSUE COMPOSITION CHARACTERISTIC OF AN ANIMAL

CROSS REFERENCE TO RELATED APPLICATIONS

This application takes priority from U.S. Provisional Patent Application Serial No. 60/039,202, filed Mar. 17, 1997, which is incorporated by reference in its entirety herein.

BACKGROUND OF THE INVENTION

1. Field of the Invention

The invention relates to the use of infrared thermographic imaging in live animals and carcasses to predict lean and fat content and composition.

2. Description of the Related Art

The estimation of tissue composition and proportion in live animals, particularly lean body mass (skeletal muscle), is difficult, and some form of allometric measurement using such parameters as weight function or surface area or skin thickness (Neilson and Jensen, 1972; Kleiber, 1975) must often be used. Ultimately, the total dissection of muscle mass, in laboratory and domestic animals, is still the most accurate method of determining lean body mass.

The ability to determine lean body mass and other tissue composition characteristics in a non-invasive manner would have substantial utility including the measurement of the physiological response of an animal to a nutritional or endocrine treatment, the prediction of an athlete's body composition in response to a training regime, sire-dam selection criteria in animal breeding programs, and carcass or lean yield predictions for slaughter animals upon which reward rates (payments) are substantially based. Given the growing concern over the consumption of saturated fats, the ability to evaluate and classify live animals and/or carcasses for lean:fat ratios would have considerable application in a value based marketing system in the animal industries (Forrest, 1995) where current visual assessment systems are considered outdated.

The measurement of lean body mass in animal carcasses has been attempted, and as discussed by O'Grady (1989) and Forrest (1995) these techniques include the use of magnetic resonance imaging spectrometry, x-ray computed tomography, visual image analysis, several types of ultrasound, electromagnetic scanning, neutron activation analysis as well as the use of optical, ultrasonic and mechanical probes. These techniques all display utility to varying degrees but all have disadvantages in terms of either cost, technical difficulties, accuracy, reliability or speed of operation. Moreover, these aforementioned techniques are predominantly conducted on the animal carcass and are thus of limited predictive value for live animals.

For lean mass assessment in live animals there are very few techniques available. Some use of electronic and tomography methods have been developed as well as ultrasound and tracer dilution techniques. Again, these procedures have usually proven to be too costly, technically difficult to operate, lacking in accuracy, or too invasive and slow to use on a large scale.

Infrared thermography is an alternative technique that has not been explored. Infrared thermography has been used in human medicine for some time for the diagnosis and study of conditions such as tumours and cardiovascular integrity (Clark and Cena, 1972) as well as hyperthermia (Hayward et al., 1975). In domestic animals, infrared thermography has also been found useful for diagnosing vascular lesions in pigs (Lamarque et al., 1975) and leg injuries in horses (Clark et al., 1972). The patent literature also discloses the use of infrared thermography for several purposes including the determination of fat content in meat post mortem (U.S. Pat. No. 3,877,818 to Button et al.), the detection of a cow in heat (U.S. Pat. No. 3,948,249 to Ambrosini), and to measure temperature differentials (U.S. Pat. No. 5,017,019 to Pompei). U.S. Pat. No. 5,474,085 to Hurnik et al. describes a method for remotely obtaining thermographic images of groups of live animals in an area such as a pen, distinguishing each animal from every other animal and the background, and using information derived from the thermographic image to determine the weight of each animal.

U.S. Pat. No. 5,458,418 to Jones et al. describes a method for detecting a high probability of producing poor meat quality in live domestic livestock, comprising the steps of:

(a) scanning the live animal with an infrared camera to produce a thermographic image;

(b) for cattle, determining the proportion of the scan falling within the test temperature range of 28–32±2° C.;

(c) for swine, determining the proportion of the scan falling within the test temperature range of 24–26±2° C.; and (d) rejecting the animal as one having a high probability of producing poor meat quality if the proportion of the scan falling within the test temperature range is lower than that falling outside the test temperature range.

U.S. Pat. No. 5,595,444 to Tong et al. describes a method for detecting poor meat quality in groups of live animals. Animals from a group of live domestic animals are scanned to produce thermographic images. The images are statistically analyzed to determine a measure of central tendency such as the mean temperature for each animal's image and for the group. A measure of dispersion from the measure of central tendency, such as standard deviation, is determined for the group. Then, animals are rejected as having a high probability of producing poor meat quality if the measure of central tendency for that animal's temperature differs from the measure of central tendency for the group by more than 0.9 standard deviations. Alternatively, up to 20% of animals are rejected, being those animals whose measures of central tendency differ the most from the measure of central tendency for the group.

However, previous research was insufficient to teach any application of infrared thermography for determining tissue composition characteristics such as lean body mass. In fact, conventional wisdom on the matter of creating predictive indexes for lean body mass discourages using any kind of temperature measurement. It is generally thought that measurement of carcass temperature is not practical in an industrial setting and that carcass temperature is uniform enough to eliminate it as one of the independent variables in a predictive model (Forrest, 1995).

Therefore, there remains a need for an accurate, inexpensive, non-invasive process for predicting tissue composition characteristics such as lean body mass in domestic animals.

SUMMARY OF THE INVENTION

The inventors have discovered that, surprisingly, the thermal expression of a warm-blooded animal is highly correlated with various tissue composition characteristics of the animal which involve the relative proportions and total quantities of different types of tissue in the animal. Importantly, the inventors have found that these correlations can be detected and quantified in infrared thermographic images taken of live animals and carcasses of the animals after slaughter.

The metabolic heat production of an animal can be detected externally by its heat loss pattern (also described as thermal expression). The thermal expression of the animal will be affected not only by the heat production of the animal, but by the quantity and proportions of tissues in the animal which act as heat sinks (absorbers of heat). Muscle tissue provides a better heat sink than fat. A number of factors are involved. Firstly, the water content of muscle tissue is greater than the water content of fat, and water itself has a high specific heat. Secondly, muscle tissue is more dense than fat and will have a greater mass per given volume. As heat capacity equals specific heat multiplied by mass, muscle tissue will have a greater heat capacity than fat. As a consequence, muscle tissue has a low insulative value and is a good conductor of heat, whereas fat has a low heat absorption capacity and is a good insulator. Skeletal muscle mass represents a large proportion of body mass (approximately 40%, Goll et al., 1977), and therefore provides a large heat sink which will be a major determinant of the thermal expression of an animal.

However, in addition to the rate of metabolic heat production and the mass of the heat sink, the thermal expression of an animal is affected by many factors which include convective, conductive, evaporative and respiratory heat loss (Robertshaw, 1977). Additional factors include hair, skin and fat cover, all of which have insulative properties. Nevertheless, despite these additional factors, the inventors have discovered that, surprisingly, they can develop predictive models which accurately relate the thermographic expression of a live animal or carcass to its muscle mass heat sink.

In making the present invention, the inventors have scanned large numbers of live domestic animals with an infrared camera from various views including the dorsal view, the lateral view and the distal view to produce infrared thermographic images. The scanned animals were subsequently processed at an abattoir, and additional thermographic images were obtained from the carcasses approximately one hour after slaughter. Various tissue composition characteristics of each animal were measured by total dissection of the carcasses into lean (muscle), bone and fat, and by known carcass grading techniques. The image area and various temperature statistical measures were calculated for each image. Using known statistical techniques such as multiple linear regression, relationships between the temperature statistics for the infrared thermographic images for the various views and the various tissue composition characteristics were determined. This has enabled the development of predictive models wherein the values of temperature statistical measures for the infrared thermographic images taken from different views of a subject animal may be input into the predictive model as input variables, and a selected tissue composition characteristic calculated as the output variable. Other variables which are not determined from the information derived from the thermographic images, such as the live weight of the animal, may be included as input variables in the predictive model.

The predictive models thus derived are particularly useful for the non-invasive determination of tissue composition characteristics of live animals. Infrared thermographic images are taken of the subject animal from each of the views needed to provide temperature data for the input variables in the predictive model. The statistical measures of temperature information from the thermographic images are then determined for each of the input variables. The predictive model is then solved to determine the value of the output variable (the tissue composition characteristic of interest, such as, for example, lean body mass) for the subject animal.

The techniques of the present invention can thus be used to determine the value of a selected tissue composition characteristic of an animal at some time prior to slaughter, for the purposes of, for instance, determining the efficacy of a nutritional regime. At the time of slaughter, testing by the techniques of the present invention might be used to determine, for example, the yield grade of the animal for carcass classification purposes. When testing is performed at the time of slaughter, it is possible to use a predictive model which includes input variables determined from thermographic images of the carcass as well as of the live animal. Further, when testing is performed at the time of slaughter, other carcass measurements, which might be difficult to perform non-invasively on the live animal, might also be included as input variables in the predictive model.

Broadly stated then, the invention provides a process for determining a tissue composition characteristic of an animal, the process comprising the steps of:
  (a) obtaining either or both of at least one infrared thermographic image of the animal while it is alive, taken from at least one view, and at least one infrared thermographic image of the carcass of the animal after slaughter, taken from at least one view, each thermographic image being capable of being represented as an array of pixels providing temperature data representative of temperature information at the corresponding part of the image;
  (b) calculating the value of at least one statistical measure of the temperature data for each thermographic image;
  (c) providing a predictive model wherein the tissue composition characteristic is included as an output variable, and the statistical measures of temperature data for each thermographic image are included as input variables; and
  (d) solving the predictive model to provide the value of the tissue composition characteristic.

An apparatus for performing the processes of the invention comprises:
  image acquisition means for obtaining either or both of at least one infrared thermographic image of said animal while it is alive, taken from at least one view, and at least one infrared thermographic image of the carcass of the animal after slaughter, taken from at least one view;
  computing and storage means for:
    storing each image as an array of pixels providing temperature data representative of temperature information at the corresponding part of the image;
    calculating the value of at least one statistical measure of the temperature data for each thermographic image;
    providing a predictive model wherein the tissue composition characteristic is included as an output variable, and the statistical measures of temperature data are included as input variables;
    solving the predictive model to provide the value of said tissue composition characteristic; and,
  output means for providing an output of the value of the tissue composition characteristic.

The present invention has application across a wide range of animal species, particularly domestic animal species. The term "animal", as used herein and in the claims, is meant to include domestic ruminant and monogastric animals, including swine (*Sus domesticus, Sus scrofa*), horses, cattle (*Bos taurus* and *Bos indicus*) and domestic ungulates such as bison, sheep, lamb, deer, moose, elk, caribou and goats. While the Examples herein demonstrate the application of the invention in cattle and hogs, as the invention involves the relationship between the thermal expression of an animal and its muscle mass (heat sink), the process should also be useful with other homoeothermic animals, including humans. Homoeothermic animals are those that maintain a relatively constant body temperature through their metabolic processes.

Within the scope of the invention, predictive models may be developed for predicting a wide range of tissue composition characteristics. As used herein and in the claims, the term "tissue composition characteristic" means any measure of the absolute quantity of a particular tissue type in an animal or a measure of the relative proportions of such tissues in an animal. Tissue types of interest include, without limitation, those particularly relevant to the commercial grading of carcasses and assessment of animals such as muscle (lean meat), fat and bone. Particularly valuable tissue composition characteristics for prediction include:

attribute of an animal carcass that is uniquely defined according to commercial practice. The process and apparatus of the present invention may be used to determine either of these types of tissue composition characteristic. An example of a user-defined tissue composition characteristic is "commercial yield", which describes how a specific commercial abattoir or packing company may process a carcass. The total yield of skeletal muscle may not be a convenient measure of quantity or commercial value of a carcass. Rather, the commercial value may best be ascertained from the yield of "primal cuts" such as flanks, ribs, rib eye steaks, blade roasts, chuck roasts, and trim. In the present invention, such unique commercial yield values may constitute the tissue composition characteristic to be determined.

It will also be apparent to those skilled in the art that predictive models may be readily developed for tissue composition characteristics that are interconvertible or reciprocal values of the tissue composition characteristics discussed above, or others. For instance, a predictive model for lean body mass of cattle is exemplified herein. Hence, by inference, it is possible to predict the non-lean body mass of the same animal which will consist predominantly of fat, bone and gastrointestinal-organ components. This non-lean

| | |
|---|---|
| Lean body mass - | The total mass of skeletal muscle in an animal. Lean body mass may also be defined as the proportion of the entire live weight of the animal represented by skeletal muscle. |
| Carcass yield - | The combined mass of skeletal muscle, bone and associated fat as a proportion of live animal weight. This value is commonly expressed as a percentage (e.g. 60% carcass yield) or as a weight relationship (e.g. 600 g/kg live weight). |
| Cuttability - | The salable yield of a carcass expressed as a proportion of live animal weight. |
| Conformation or Body Scores - | The degree of apparent muscling in a live animal. For example, a breeding or genetic company would use a different conformation score for a well finished Limousine breeding bull compared to an under finished Long Horn bull. The conformation score can also be used, for example, by animal herdsmen for comparing the relative fitness or condition of cattle displaying more flesh cover or less flesh cover. |
| Grade Fat - | The depth (mm) of subcutaneous fat at some repeatable anatomical site along the dorsal surface of the animal. Typically, measurement is made at the 12th rib distal to the atlas vertebrae and approximately 10 cm lateral to the dorsal mid-line. The abattoir or packing company may vary the measurement site. This measure is typically taken either by direct measurement with a ruler on a carcass or also with technology such as an ultra sound probe. |
| Lean Yield - | The lean yield of muscle expressed as g/kg of cold side weight × side weight of cold carcass. Lean yield is equivalent to lean body mass. |
| Muscle Score - | A mathematical value obtained by making a measurement (ruler or ultrasound measurement) of the rib eye area (typically length and width) on the longissimus dorsi muscle at a fixed anatomical site (again, typically the 12th rib). |
| Rib Eye Area - | The surface area of a cross section of the longissimus dorsi muscle, typically again at the 12th rib. This is usually obtained by either tracing directly onto a sheet of waxed paper and then using a planometer system to elucidate or measure or, alternatively, this is obtained with a mathematical measure of length and width to measure or estimate area. In the pig, the comparable measurement is the loin eye area. |
| Average Fat - | A mathematical average of usually three fat measurements taken along the dorsal surface of the animal measured either on the carcass or by ultrasound. |
| US Fat - | A measure of fat depth or quantity (subcutaneous and/or marbling intramuscular fat) commonly used in the US to classify carcasses into categories such as prime, choice, or select. US fat thus denotes both fat thickness and degree of marbling. |

The "tissue composition characteristics" described above include those that relate to specific measurements that can be taken directly from a live animal or carcass and are independent of commercial requirements or grading standards as well as those that describe a commercially important value may be useful in certain applications. Similarly, the prediction of carcass yield, as described in Example 2, provides, by inference, the measure of non-carcass yield, that is to say the mass of the gastrointestinal tract, which again may be a useful measure in particular circumstances.

The invention may also be used to determine tissue composition characteristics which are non-parametric, and are assessed on a rank-scale. Such characteristics include, without limitation, animal or carcass grading assessments, which may vary on a country-by-country basis, and which may not be adapted to absolute numerical descriptions. For instance, as discussed in the Examples herein, Canadian beef cattle in the top grades are distinguished as AAA, AA, and A-grades on the basis of the relative proportion of marbling (intramuscular fat) in the meat, without prescribing absolute fat measures.

The sample population of animals used to develop the predictive model is preferably a group of animals of the same species, the group containing a sufficient number of animals that a statistically significant relationship or correlation between one or more of the selected input variables and the tissue composition characteristic (output variable) of interest can be determined. The sample population may contain as few as three animals, and more preferably greater than ten animals, and still more preferably, greater than 100 animals.

The infrared thermographic images of the animals are obtained using standard, commercially available infrared thermographic cameras, equipment and related computer software. The term "infrared thermographic image" as used herein and in the claims, is meant to include a scan output in the form of either or both of a visual image and corresponding temperature data. The output from infrared cameras used for infrared thermography typically provides an image comprising a plurality of pixel data points, each pixel providing a temperature data point which can be further processed by computer software to generate for example, mean temperature for the image, or for a discrete area of the image, by averaging the data points over the number of pixels.

The views of the animals from which the infrared thermographic images are obtained may include, without limitation, the dorsal (top), lateral (side), distal (rear), ventral (bottom) and proximal (front) view of the live animal or carcass. The images taken from each view may not cover the entire animal surface from that view. Rather, the image may include only a portion of the lateral, dorsal, ventral, proximal or distal surface of the animal or carcass.

Once infrared thermographic images are obtained for each animal in the sample population from the selected views, values for selected statistical measures are calculated for the temperature data, to provide a set of data for each of the input variables. As discussed previously, thermographic images may also be obtained from the carcasses of the animals from selected views. The images of the carcasses are obtained within about 24 hours after slaughter, and preferably within about one hour after slaughter. Selected statistical measures of the temperature data obtained from the thermographic images of the selected views of the carcasses may also form input variables.

Preferred statistical measures include measures of central tendency, measures of dispersion, and measures of total temperature. The term "measure of central tendency" as used herein and in the claims is a statistical measure of a point near the centre of a group of data points. Without limitation, the term includes the mean, median and mode. The term "measure of dispersion" as used herein and in the claims is meant to include statistical measures of spread from the measure of central tendency for the group, and include without limitation, variance, standard deviation and coefficient of variation. Definitions of these statistical terms may be found in standard statistic texts, one such text being Steel and Torrie (1980), which definitions are incorporated herein by reference. As used herein and in the claims, "total temperature" is the mean temperature of an infrared thermographic image×image area expressed in number of pixels (e.g. if mean temperature=20° C. and the image area=200 pixels, then total temperature=20° C.×200=4000° C.).

The selection of input variables may include measures that are obtained independently of the infrared thermographic images. Such variables include, without limitation, animal live weight, carcass weight, and fat thickness. "Live weight" typically refers to the live weight of an animal pre-slaughter. Carcass weight is typically differentiated into "hot carcass weight" and "cold carcass weight". Hot carcass weight is typically measured within one hour after slaughter, whereas cold carcass weight would typically be measured 24–48 hours after slaughter and after the carcass has been cooled by refrigeration.

The actual value for the tissue composition characteristic of interest is measured for each animal in the sample population to provide a set of data for the output variable. The method used to measure the values for the output variable for the animals in the sample population will depend on the nature of the selected tissue composition characteristic. For instance, where the output variable is the lean body mass of the animal, the lean mass may be determined by total dissection into lean, bone and fat according to known or accepted methods (Jones et al., 1995).

Using the data obtained for each of the input variables and the data obtained for the output variable, a relationship between the input variables and the output variable is determined to create a predictive model by which the value of the selected tissue composition characteristic for a subject animal can be predicted from the values calculated for the input variables for the subject animal. As used herein and in the claims, a "predictive model" means a predictive outcome or hypothesis that is based on an inductive process requiring empirical observations; "input variables" are the empirical observations used in such a model, and the "output variable" is the predictive value or hypothesized value. The output variable is then tested empirically against actual or direct measures of outcome. For example, dissected lean body mass or carcass lean yield is compared for accuracy against a correlation value. Any of a number of known statistical techniques can be used to determine the relationship between the input variables and the output variable to arrive at a predictive model. These techniques include, without limitation, multiple linear regression, cluster analysis, discriminant analysis, and Artificial Neural Network learning. In many statistical techniques, the input variables are known as the independent variables, and the output variable is known as the dependent variable.

Once a predictive model for a particular tissue composition characteristic has been determined, a value for that tissue composition characteristic can be predicted for other animals for which the sample population used to build the predictive model is representative. For each subject animal, values are determined for each of the input variables in the predictive model. Depending on the predictive model used, these values may be determined from the live animal prior to slaughter, from the animal carcass post-slaughter, or both. Values for input variables not representing temperature information (eg. animal live weight) can be obtained by the appropriate known measurement technique. Thermographic images are obtained of the animal from each view required to provide temperature information for the predictive model to be used and are stored in digitized form. As noted above, the thermographic images obtained may include images of the animal carcass obtained within about 24 hours after slaughter. Using commercially available statistics software, the appropriate statistical measures are determined for the temperature data provided by each image to provide a value for each input variable in the predictive model. The value of each input variable for the subject animal is substituted into the predictive model which has been programmed into known computing and storage means, and the predictive model is solved to provide a prediction of the value of the tissue composition characteristic of interest for the subject animal. Known output means can be used to provide an output of the value of the tissue composition characteristic of interest in a form suitable for the nature of the commercial application.

In an exemplified case, a preferred predictive model is provided for predicting lean body mass in cattle. The predictive model is generally defined as:

$$Y=\beta_0+\beta_1 X_1+\beta_2 X_2+\beta_3 X_3+\beta_4 X_4+\beta_5 X_5+\beta_6 X_6+\beta_7 X_7+\beta_8 X_8+\beta_9 X_9$$

wherein Y=lean body mass, $\beta_0$–$\beta_9$ are coefficients, $X_1$=total temperature of the dorsal view of the live animal, $X_2$ is the standard deviation of temperature of the dorsal view of the live animal, $X_3$ is the total temperature of the distal view of the live animal, $X_4$ is the standard deviation of temperature of the distal view of the live animal, $X_5$ is the total temperature of the lateral view of the live animal, $X_6$ is the standard deviation of temperature of the lateral view of the live animal, $X_7$ is the total temperature of the lateral view of the carcass 1 hour after slaughter, $X_8$ is the standard deviation of the temperature of the lateral view of the carcass 1 hour after slaughter, and $X_9$ is the live weight of the animal.

DETAILED DESCRIPTION OF THE PREFERRED EMBODIMENT

Figure 1:
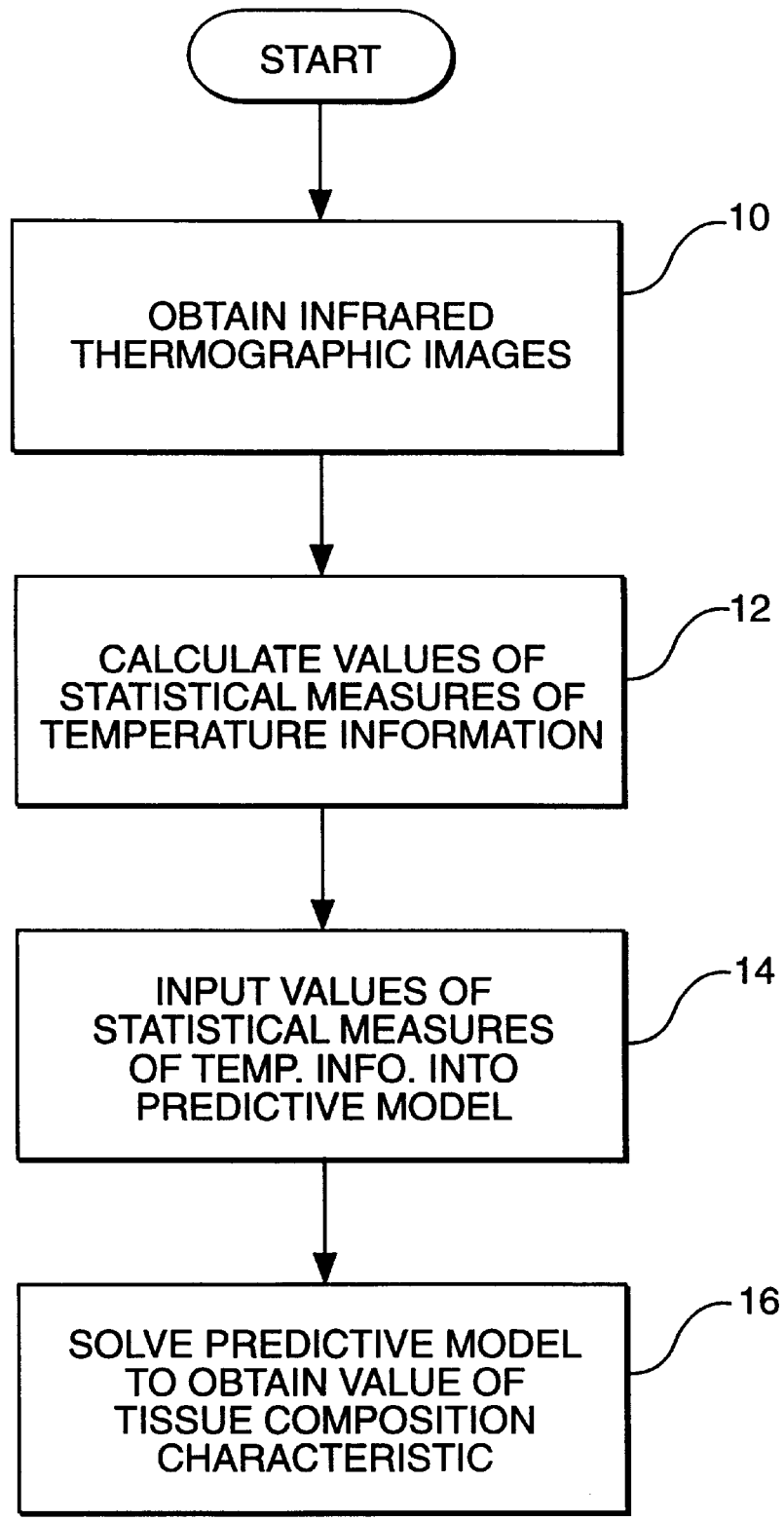
FIG. 1 depicts a predictive model for determining a tissue composition characteristic (output variable).

Infrared thermographic equipment and related computer software used in association with the present invention is known in the art. The infrared camera may be, for example, an Inframetrics 760 broadband camera (Inframetrics Corp. North Billerica, Mass.). This camera can be fitted with a number of different lenses such as a 0.5×lens. Suitable software for analysing the thermographic images includes Thermogram image software (Inframetrics Inc., North Billerica, Mass.) and Viewscan Software (Viewscan Ltd., Concord, Ont).

In developing a predictive model of the invention, each animal in a sample population is scanned from a range of about 1–3 m. The preferred range is 175–185 cm. The thermographic images should be obtained from steady-state unstressed animals. Stress in animals can be caused by such factors as transport and mixing of animals that have been reared in different groups. Stressed animals exhibit aberrant thermal expression which may interfere with the collection of data suitable for making the predictive models of the invention.

Infrared thermographic images are collected from a number of views which may include the dorsal (top), distal (rear), lateral (side), proximal (front) and ventral (bottom) views of the animal. The scans showing the greatest utility, in the experience of the inventors, are the dorsal, distal and lateral views. The images can include the whole animal or can be limited to a portion of the animal. Images from the various selected views are preferably taken of each animal both before slaughter, and of each animal carcass within approximately 24 hours after slaughter.

The image area and the selected image temperature statistics are calculated for each of the infrared thermographc images obtained of the sample population. An uncalibrated, digitized thermographic image (the image as obtained, without further processing) may consist of, say, 135×256 pixels. The relative radiant surface temperature represented by each pixel of the uncalibrated image may be represented by assigning each pixel a numerical value in the range from, for instance, 0 to 255. The pixel values are mapped to actual Celsius temperature by relating them to the maximum and minimum temperature settings of the infrared camera through the following formula:

$$\text{Actual temperature} = \frac{(\text{maximum temperature setting} - \text{minimum temperature setting})}{256} \times \text{pixelvalue pixel}$$

To assist a human operator viewing the infrared thermographic images on a computer monitor, pseudo-colours can be generated by assigning a specific colour to all pixels with temperature values within a certain range. For example, purple may identify pixels representing temperatures less than 16° C., blue for temperatures from 16 to 19° C., and light blue for temperatures from 19 to 21° C.

Though the entire image may be processed, preferably a matrix within each image, measuring about 50×100 pixels, is selected for further analysis. Let $t_{ij}$ represent temperature value in the I-th row and j-th column of this selected matrix of temperature, I from 1 to r and j from 1 to c, and r=50 rows and c=100 columns. Sample mean, standard deviation, minimum, maximum and mode of this temperature matrix are calculated as follows:

$$\text{sample mean} = \bar{t} = \frac{\sum_{i=1}^{r}\sum_{j=1}^{c} t_{ij}}{r \times c}$$

$$\text{sample standard deviation} = \sqrt{\frac{\sum_{i=1}^{r}\sum_{j=1}^{c} (t_{ij} - \bar{t})^2}{r \times c - 1}}$$

The sample mode is the most frequent temperature.

The selected statistical measures for each selected view become input variables used in the development of the predictive model. As discussed previously, other input variables, representing animal properties which may not be derived from the infrared thermographic analysis, may be included in developing the predictive model. Such additional input variables include, without limitation, properties which are size or quantity measurements such as animal live weight, carcass weight and fat thickness. Standardized procedures for measuring various physical characteristics of live animals and carcasses are known, allowing consistent measurements of these additional input variables to be obtained (Jones et al., 1995). These additional input variables can also include animal properties that are not size or quantity measurements, such as, for example the sex of the animal.

A value for the selected tissue composition characteristic (output variable) of each scanned animal in the sample population is measured. The measurement technique and units in which the measurement is expressed will vary depending on the tissue composition characteristic selected. For instance, if the output variable is lean body mass, this may be measured by total dissection of the carcass, and expressed in kilograms, or as a proportion of live weight. Conversely, if the output variable is a non-parametric measure such as a beef grading distinction between AAA-grade and AA/A-grade carcasses, measurement of the value of this variable in the sample population might be determined by visual observation of rib eye marbling, and the value expressed as a rank or grade.

Using the accumulated data, a relationship between the statistical measures for the selected infrared thermographic image views and additional input variables such as live weight, and the selected tissue composition characteristic (output variable) is determined to provide a predictive model whereby, given a value for each of the input variables in the model, the value of the output variable can be predicted. Thus, as shown in the figures once a predictive model for a selected tissue composition characteristic for a sample population has been established, the value for the selected tissue composition characteristic for a subsequent animal for which the sample population is statistically appropriate can be predicted by: (a) obtaining infrared thermographic images of the subject animal from the selected views 10; (b) calculating a value for each selected statistical measure to obtain a data point for each input variable for the subject animal 12; (c) substituting the data points obtained for each input variable for the subject animal into the predictive mode 14; and (d) calculating the predicted value of the selected tissue composition characteristic for the subject animal 16, see FIG. 1.

The relationship between the input variables and the output variable can be determined by any of a number of known statistical methods such as multiple linear regression, Artificial Neural Net learning, cluster analysis and discriminant analysis. In a preferred embodiment, the multiple regression procedure of SAS (SAS Institute Inc., Cary N.C.) is used. Where there are multiple input variables, a solution utilizing matrix algebra may be used. For instance, where nine input variables are being analysed, and the output variable is lean body mass, the multiple regression model may be:

$$y_j = a + b_1 x_{1j} + b_2 x_{2j} + b_3 x_{3j} + b_4 x_{4j} + b_5 x_{5j} + b_6 x_{6j} + b_7 x_{7j} + b_8 x_{8j} + b_9 x_{9j} + e_j$$

$$= a + \sum_{i=1}^{9} b_i x_{ij} = e_j$$

where:

$y_j$=the percentage lean body mass of the j-th animal, j=1,2 ... n, a=the overall mean $b_i$=the i-th regression coefficient, i=1, 2 ... 9, $x_j$=the j-th predictor variable, $e_j$=random error associated with the j-th observation.

The following matrix and vectors are defined:

$$x = \begin{bmatrix} 1 & x_{11} & x_{21} & \ldots & x_{91} \\ 1 & x_{12} & x_{22} & \ldots & x_{92} \\ \vdots & \vdots & \vdots & \vdots & \vdots \\ 1 & x_{1n} & x_{2n} & \ldots & x_{9n} \end{bmatrix}, y = \begin{bmatrix} y_1 \\ y_2 \\ \vdots \\ y_n \end{bmatrix}, e = \begin{bmatrix} e_1 \\ e_2 \\ \vdots \\ e_n \end{bmatrix}, \text{and } b = \begin{bmatrix} b_1 \\ b_2 \\ \vdots \\ b_n \end{bmatrix}$$

The complete set of equations is:

$y=Xb+e$ with $E(y)$, $E(e)=0$ and $\mathrm{var}(e)=\sigma^2 I$, where E denotes the expectation operator and $\sigma^2$ is a constant.

The regression coefficients b is estimated as:

$b=(X'X)^{-1}X'y$

The prediction is:

$$y = a + \sum_{i=1}^{9} b_i x_{ij}$$

The invention is further illustrated by the following non-limiting examples.

EXAMPLE 1

The objective of this example was to determine whether infrared thermography could be used to predict the lean body mass of cattle.

Sixteen market weight (500 kg) crossbred steers raised at the Agriculture and Agri-Food Canada Lacombe Research Centre (Lacombe, Alberta, Canada) beef unit facilities on conventional cereal-silage diets were used in this study. The cattle were transported to the Lacombe Research Centre Meats Research Facility in the morning and within two hours of arrival they were scanned by an infrared camera (Inframetrics model 760 with a 0.5×lens). Scans were obtained from dorsal, lateral and distal views of the live animals at a distance of 175–193 cm. TPI image software (Ottawa, Canada) was used for the subsequent resolution and printing of the individual thermographs as described in Example 2 herein. The live weight of the animals was also determined.

The animals were subsequently processed at the Lacombe Research Centre Meats Research Facility abattoir and thermographic scans were obtained of the carcasses of the animals from the lateral view approximately one hour after slaughter. The total lean body mass for the animals was measured by total dissection into lean, bone and fat according to the methods described by Jones et al. (1987).

The image area and values for temperature statistics including the mean, mode and standard deviation as well as the product of the image mean temperature×image area (previously defined as total temperature) were calculated for each of the infrared images. For each animal, the following information was compiled:

1. an animal identification number;
2. the live weight of the animal in kilograms;
3. lean body mass of the carcass as determined by dissection;
4. for the image of the dorsal view of the live animal, the image area in cm$^2$, maximum image temperature, mean image temperature, minimum image temperature, mode of image temperature, standard deviation of image temperature, and total temperature for image;

5. for the image of the distal view of the live animal, the image area in cm², maximum image temperature, mean image temperature, minimum image temperature, mode of image temperature, standard deviation of image temperature, and total temperature for image;
6. for the image of the lateral view of the live animal, the image area in cm², maximum image temperature, mean image temperature, minimum image temperature, mode of image temperature, standard deviation of image temperature, and total temperature for image; and,
7. for the image of the lateral view of the carcass of the animal one hour after slaughter, the image area in cm², maximum image temperature, mean image temperature, minimum image temperature, mode of image temperature, standard deviation of image temperature, and total temperature for image.

The lean body mass was not determined for the carcasses of four of the 20 animals. These were condemned animals that did not undergo further abattoir processing.

The degree of linear association between the selected statistical measures or groups of the selected statistical measures of the infrared images of the selected views and animal live weight (input variables) and lean body mass (output variable) was determined using multiple regression procedures as defined by Steel and Torrie (1960). The degree of linear association was calculated as the coefficient of determination ($r^2$ value) shown in Table 1. The value of $r^2$ defines the fraction of the total variation that can be ascribed to the linearity relationship. As shown in Table 1, the highest $r^2$ value for any set of input variables tested was 0.89. This indicates that 89% of variation in lean body mass can be explained by the linearity relationship between the set of input variables tested and lean body mass.

Using the set of predictors (input variables) exhibiting the highest $r^2$ value, the following predictive model for predicting lean body mass in cattle was determined using multiple regression procedures as defined by Steel and Torrie (1960):

% lean body mass=566.8795+0.0014$X_1$−30.9181$X_2$0.0015$X_3$+ 29.5325$X_4$+0.0009$X_5$−15.9213$X_6$+0.0005$X_7$−31.1438$X_8$− 0.05625$X_9$ wherein $X_1$ is the total temperature of the dorsal view of the live animal, $X_2$ is the standard deviation of temperature of the dorsal view of the live animal, $X_3$ is the total temperature of the distal view of the live animal, $X_4$ is the standard deviation of temperature of the distal view of the live animal, $X_5$ is the total temperature of the lateral view of the live animal, $X_6$ is the standard deviation of temperature of the lateral view of the live animal, $X_7$ is the total temperature of the lateral view of the carcass one hour after slaughter, $X_8$ is the standard deviation of the temperature of the lateral view of the carcass one hour after slaughter, and $X_9$ is the live weight of the animal.

To use this predictive model in practice, thermographic images of the animal for which lean body mass is to be determined are taken from each of the dorsal, distal and lateral views of the animal prior to slaughter. The live weight of the animal is also measured. About one hour after slaughter, a thermographic image is obtained of the lateral view of the carcass. The appropriate statistical measures are determined for the temperature data provided by each image to provide a value for each input variable. The value of each input variable for the subject animal are substituted into the predictive model and the predictive model solved to provide a prediction of the lean body mass of the animal.

As noted above, this example demonstrating the prediction of lean body mass in cattle was based on a cut-out study of 16 animals. The cost and labour involved in studies

TABLE 1

Coefficients of determination ($r^2$ values) of Lean Body Mass Predictors With Actual Dissected Lean Mass in 500 kg Beef Steers

| Measurement | $r^2$ Value |
|---|---|
| mean temp. of dorsal view of live animal + stnd. dev. of temp. of dorsal view of live animal | 0.37 |
| mean temp. of distal view of live animal + stnd. dev. of temp. of distal view of live animal | 0.49 |
| mean temp. of lateral view of live animal + stnd. dev. of temp. of lateral view of live animal | 0.30 |
| mean temp. of dorsal view of live animal + stnd. dev. of temp. of dorsal view of live animal + live weight | 0.46 |
| mean temp. of distal view of live animal + stnd. dev. of temp. of distal view of live animal + live weight | 0.68 |
| mean temp. of lateral view of live animal + stnd. dev. of temp. of lateral view of live animal + live weight | 0.47 |
| mean temp. of lateral view of carcass 1 h after slaughter + stnd. dev. of temp. of lateral view of carcass 1 h after slaughter | 0.15 |
| mean temp. of lateral view of carcass 1 h after slaughter + stnd. dev. of temp. of lateral view of carcass 1 h after slaughter + carcass weight | 0.40 |
| mean temp. of dorsal view of live animal + mean temp. of distal view of live animal + mean temp. of lateral view of live animal + stnd. dev. of temp. of the dorsal view of the live animal + stnd. dev. of temp. of distal view of live animal + stnd. dev. of temp. of lateral view of live animal + live weight | 0.74 |
| total temp. of dorsal view of live animal + total temp. of distal view of live animal + total temp. of lateral view of live animal + stnd. dev. of temp. of the dorsal view of the live animal + stnd. dev. of temp. of distal view of live animal + stnd. dev. of temp. of lateral view of live animal + live weight | 0.72 |
| total temp. of dorsal view of live animal + total temp. of distal view of live animal + total temp. of lateral view of live animal + total temp. of lateral view of carcass 1 h after slaughter + stnd. dev. of temp. of the dorsal view of the live animal + stnd. dev. of temp. of distal view of live animal + stnd. dev. of temp. of lateral view of live animal + stnd. dev. of temp. of lateral view carcass 1 h after slaughter + live weight | 0.89 | involving the total dissection of large animal carcasses such as cattle to determine lean body mass place constraints on the size of sample populations that can be used in a research setting. In a commercial setting, it may be possible to include data from a much larger cut-out study. It will be appreciated that those skilled in the art that superior accuracy may be achieved using the processes of the present invention with predictive models based on larger sample populations, ideally around 1500 animals.

It is apparent in Table 1 that high $r^2$ values were obtained with sets of input variables other than the preferred set of input variables used to derive the above predictive model. For instance, $r^2$ values of 0.68, 0.72 and 0.74 were also obtained with different sets of input variables. Those skilled in the art will appreciate that within the scope of the invention, there may be applications where a lower degree of accuracy in the prediction of the tissue composition characteristic of interest will be acceptable and it may therefore be possible to use a predictive model with fewer input variables. For example, although greater accuracy might be achieved in predicting lean body mass in cattle if statistical measures of temperature data obtained from the lateral view of the carcass one hour after slaughter are included in the predictive model, circumstances may make it impractical to obtain thermographic images of the cattle after slaughter. It may prove sufficient in those circumstances to use a predictive model that does not include statistical measures of temperature data obtained from the lateral view of the carcass one hour after slaughter as input variables, even if such a model does not provide the optimum degree of predictive accuracy, in order to avoid the need to obtain thermographic images in the post-mortem environment.

EXAMPLE 2

The objective of this example was to determine whether infrared thermography can be used to distinguish differences in carcass fat composition or grade in live animals.

A total of 866 crossbred steers and heifers weighing approximately 500 kg weight were dorsally scanned with an infrared camera within one hour prior to slaughter in the antemortem holding area at the IBP Inc. beef abattoir located at Brooks, Alberta, Canada. The infrared thermographic images were taken with an Inframetrics 760 broadband camera (Inframetrics Corp. North Billerica, Mass.). Subsequent resolution and printing of the individual thermographs was accomplished using Viewscan software (Viewscan Ltd, Concord, Ontario, Canada) as set out below.

The video signal from the camera was converted to digital data with an A/D converter before being processed by a computer as follows. The image was saved as a raw, uncalibrated data file. The area of the image itself was divided into pixels. The raw pixel data was digital data proportional to voltage signals from the infrared camera. In order to analyse the thermograph, the digital data was converted to temperature data using a calibration procedure with the Viewscan software. After calibration, the pixels were displayed in fifteen different colours plus a background colour, representing fifteen temperature ranges of 1.2+/−0.2° C., ranging from 15.0 to 32.0° C.

The Viewscan software allowed for analysis of the pixel data by different zones or by the entire image. The following information was obtained for each image using the Viewscan software: absolute pixel counts and pixel counts as a percentage of the total pixels in the image falling into each temperature range; maximum and minimum temperatures in the image; the overall range of temperatures in the image; the median, the mean, and standard deviations of temperatures in the image; and the total area of the image (in pixels).

The live weight of each animal was also measured prior to slaughter. After slaughter, the carcasses from all animals were classified according to Canadian beef grading standards (Alberta Agriculture Feedlot Handbook, 1997) and all carcasses were in the highest standards or A grade categories. The percentage yield of each carcass was also determined. As described previously, carcass yield is the combined mass of skeletal muscle, bone and associated fat as a proportion of live animal weight and is commonly expressed as a percentage (e.g. 60% carcass yield) or as a weight relationship (e.g. 600 g/kg live weight). The carcass classification, average infrared thermography dorsal temperatures and standard errors (SE) are shown in Table 2.

TABLE 2

Average infrared dorsal temperatures +/− SE for three classes of cattle

| Carcass Classification | A | AA | AAA |
| --- | --- | --- | --- |
| sample size | n = 143 | n = 522 | n = 201 |
| mean live animal dorsal temperature (° C.) | 26.7[a] | 26.85[a] | 27.6[b] |
| +/− standard error | 0.22 | 0.11 | 0.18 |

[a,b]Statistically different at P < 0.01

Apparent in Table 2 is the observation that the animals producing carcasses classed as triple A (AAA) were observed to display infrared thermography temperatures that were statistically different from cattle displaying carcasses of either single A(A) or double A (AA) grades.

As described in the Canadian Beef Grading system, carcasses with different grade classification between A-AA and AAA differ in fat composition. A-grade cattle exhibit trace levels of marbling. AA-grade cattle exhibit slight levels of marbling, and AAA-grade cattle exhibit small levels (>slight) of marbling. Grades A, AA and AAA are otherwise substantially identical. Marbling is the common name given to the flecks of intramuscular fat exposed on the cut surface of a muscle, typically viewed on the longissimus dorsi muscle, cut between the 11th and 12th rib of the carcass. Thus, animals having different levels of intramuscular fat were distinguished by infrared thermography. Hence, this example illustrates that infrared thermography can be used on live animals to differentiate fat composition.

Given that a statistically significant distinction in mean temperature based upon single dorsal scans of each animal was detected between A/AA and AAA-grade cattle having slightly different levels of marbling, it is apparent that it is possible to develop predictive models in which the relative or absolute fat composition of a live animal may be predicted from infrared thermography data. This will hold particularly true if the input variables include various statistical measures other than only the mean for infrared thermographic images from views other than the dorsal view as well as other non-thermographic measures.

Though in a commercial setting, a predictive model would likely be developed which might include input variables derived from thermographic data obtained from other views of the animal than the dorsal view, and might also include input variables derived from non-thermographic data such as animal weight, it is nevertheless possible to provide an example of a very simple predictive model based on the observed mean temperature distinction in the dorsal scans of A,AA versus AAA-grade cattle. Such a predictive model that might be applied would be Group 1 (A, AA)=Temperature (dorsal)<26.85±0.11° C.

Group 2 (AAA)=Temperature (dorsal)>27.6±0.18° C.

Such a predictive model would have application in Canada, for instance, where there is only a small price premium for AAA-grade cattle over AA or A-grade cattle. In the United States, the Department of Agriculture grade equivalent to Canada-AAA is termed choice or prime, and there is a price premium for such animals. If a Canadian producer were to determine from the application of the present invention using the above predictive model which of its cattle were likely to grade AAA rather than AA or A, it would be able to market the AAA grade animals to the United States to realize the price premium.

EXAMPLE 3

It was the objective of this example to determine whether infrared thermography values collected from live pigs would display a statistically significant relationship with the lean body mass in pigs, as was determined to be the case with other species such as cattle. Such information could be used in predictive models as provided in Example 1.

27 market weight (100 kg) crossbred pigs raised at the swine unit of the Agriculture and Agri-Food Canada Lacombe Research Centre at Lacombe, Alberta were used in this trial. The pigs were transported to the Lacombe Research Centre Meats Research Facility in the morning and within two hours of arrival were scanned with an infrared camera (Inframetrics model 760 with a 0.5×lens). Scans were obtained from the dorsal surface only. TPI image software (Ottawa, Canada) was used for the subsequent resolution and printing of the individual thermographs as described in Example 2.

The pigs were subsequently processed at the Meats Research Facility and the total lean body mass for the animals was directly measured by total dissection into lean, bone, and fat according to the methods described by Dugan et al. (1997).

The image area and values for temperature statistics including the mean, mode and standard deviation were determined. Table 3 provides the values for the lean yield of muscle from these animals (calculated as the lean dissected weight expressed as g/kg of cold side weight×the side weight of the cold carcass) and the total temperature (image area in number of pixels×mean image temperature). The degree of association between the lean yield value and the total temperature is expressed in Table 3 as the coefficient of linear correlation (r) determined by Pearson Correlation Coefficients (SAS, 1985). In Table 3, r expresses the strength of the linear relationship between lean yield and total temperature. The value of r always ranges between −1 and 1 inclusive. That is, $-1 \leq r \leq 1$. When r=1, there is a perfect positive correlation. For a perfect positive correlation with r=1, in a scatter diagram plotting dorsal total temperature against lean yield, all the points would lie on a straight line rising upward to the right. A value of r=−1 means that there is a perfect negative correlation and that all the points lie on a straight line falling downward to the right. Any value of r in the vicinity of +1 or −1 implies that the points are scattered closely around a straight line. Table 3 reports an r value of 0.72 at P=0.0001. It is therefore evident in Table 3 that there is a highly statistically significant probability that total temperature is correlated with lean yield in the pig. The thermal expression of a pig having been demonstrated to be closely associated with its lean yield, it is apparent to those skilled in the art that the processes of the present invention could be used to develop predictive models for tissue composition characteristics in pigs.

The results presented in Table 3 can be used to derive a predictive model wherein total temperature of the dorsal view of the live pig is the input variable, and lean yield is the tissue composition characteristic forming the output variable. As with Example 2, those of skill in the art will recognize, based on the results reported in Example 1, that the accuracy of the predictive model in pigs could be increased by including additional input variables constituting statistical measures of temperature data obtained from thermographic images of views of the animals other than the dorsal view as well as non-temperature related input variables such as live animal weight.

TABLE 3

Lean yield, total temperature and correlation between lean yield and total temperature in market weight pigs.

| Lean Yield[1] (kg) mean ± stand. dev. | total temperature[2] mean | r Value |
|---|---|---|
| 43.5 ± 3.76 | 233,823° C. | 0.72 |

[1]lean yield of muscle as g/kg of cold side weight × side weight of cold carcass
[2]image area in pixels × mean image temperature
[3]P = 0.0001

LIST OF REFERENCES

Clark, J. A. and Cena, K. 1972. Thermographic measurements of the surface temperatures of animals. J. of Mammalogy 54: 1003–1007.

Dugan, M. E. R., A. K. W. Tong, J. P. Carlson, B. R. Schricker, J. L. Aalhus, A. L. Schaefer, A. P. Sather, A. C. Murray and S. D. M. Jones. 1997. The effects of porcine somatotropin, gender and porcine stress syndrome on growth, carcass composition and pork quality. Canadian J. Animal Science. 77:233–240.

Forrest, J. C. 1995. New techniques for estimation of carcass composition. pp 157–171 In. Quality and grading of carcasses in meat animals Ed. By. S. D. M. Jones. CRC Press. New York.

Goll, D. E., Stromer, M. H. and Robson, R. M. 1977. Skeletal muscle, nervous system, temperature regulation and special senses. P 504–548. In. Dukes Physiology of domestic animals. 9th ed. Ed by M. J. Swenson. Comstock Pub. Cornell Univ. Press. Ithaca.

Hayward, J. A., Eckerson, J. D. and Collis, M. 1975. Thermal balance and survival time prediction of men in cold water. Can. J. Physiol. Pharmacol. 53: 21–32.

Jones, S. D. M ed. 1995. Quality and Grading of Carcasses of Meat Animals. CRC Press. New York.

Jones, S. D. M., Tong, A. K. W. and Robertson, W. M. 1987. The effect of carcass grade and sex on lean content of beef carcasses. Can. J. Anim. Sci. 67: 205–208.

Kleiber, M. 1975. The fire of life. R.E. Krieger Pub. Comp. New York.

Neilson, N. P. and Jensen, C. R. 1972. Measurement and statistics in physical education. Woodsworth Pub. Comp. Inc. Belmont, Calif.

O'Grady, J. F. 1989. New techniques in pig carcass evaluation. Editor EAAP Pub. No 41. Pudoc, Wageningen.

Robertshaw, D. 1977. Environmental Physiology II. Univ. Park Press. Baltimore.

SAS Institute Inc. 1985. SAS User's Guide: Statistics. 5th ed. SAS Institute, Inc. Cary, N.C.

Steel, R. G. D. and Torrie, J. H. 1960. Principles and Procedures of Statistics. McGraw-Hill Book Company Ltd. New York.

Steel, R. G. D. and Torrie, J. H. 1980. Principles and Procedures of Statistics, A Biometrical Approach. 2d edition. McGraw-Hill Book Company Ltd. New York.

All publications mentioned in this specification are indicative of the level of skill of those skilled in the art to which this invention pertains. All publications are herein incorporated by reference to the same extent as if each individual publication was specifically and individually indicated to be incorporated by reference.

Although the foregoing invention has been described in some detail by way of illustration and example for purposes of clarity of understanding, it should be understood that certain changes and modifications may be practised within the scope of the appended claims.

What is claimed is:

1. A process for determining the value of a tissue composition characteristic of an animal, comprising the steps of:
    obtaining either or both of at least one infrared thermographic image of said animal while it is alive, taken from at least one view, and at least one infrared thermographic image of the carcass of said animal after slaughter, taken from at least one view, wherein each of said obtained thermographic images is capable of being represented as an array of pixels providing temperature data representative of temperature information at the corresponding part of the image;
    calculating the value of at least one statistical measure of the temperature data for each thermographic image;
    providing a predictive model wherein said tissue composition characteristic is included as an output variable, and said statistical measures of temperature data for each thermographic image are included as input variables; and
    solving said predictive model to provide the value of said tissue composition characteristic.

2. The process of claim 1, wherein said statistical measures are selected from the group consisting of a measure of central tendency, a measure of dispersion, and a total temperature.

3. The process of claim 1, wherein, in said image obtaining step, at least one infrared thermographic image is obtained of said animal while it is alive, taken from at least one view.

4. The process of claim 1, wherein, in said image obtaining step, at least one infrared thermographic image is obtained of the carcass of said animal after slaughter, taken from at least one view.

5. The process of claim 1, wherein said tissue composition characteristic is selected from the group consisting of lean body mass, cuttability, degree of marbling, percent carcass yield, lean yield, rib eye area, loin eye area, subcutaneous fat thickness and grade classification.

6. The process of claim 1, comprising the further step of:
    obtaining the value of at least one property of said animal, either before or after slaughter, that does not provide temperature information, and wherein said property is included as an input variable in said predictive model.

7. The process of claim 6, wherein said property that does not provide temperature information is the live weight of said animal.

8. The process of claim 7, wherein said thermographic images comprise an image of the distal view of the live animal; and said statistical measures comprise the mean temperature of the image of the distal view of the live animal and the standard deviation of temperature of the image of the distal view of the live animal.

9. The process of claim 7, wherein said thermographic images comprise an image of the dorsal view of the live animal, an image of the lateral view of the live animal, and an image of the distal view of the live animal; and said statistical measures comprise the total temperature of the image of the dorsal view of the live animal, the total temperature of the image of the distal view of the live animal, the total temperature of the image of the lateral view of the live animal, the standard deviation of temperature of the image of the dorsal view of the live animal, the standard deviation of temperature of the image of the lateral view of the live animal, and the standard deviation of temperature of the image of the distal view of the live animal.

10. The process of claim 9, wherein said thermographic images further comprise an image of the lateral view of the carcass of the animal after slaughter; and said statistical measures further comprise the standard deviation of temperature of the image of the lateral view of the carcass of the animal after slaughter, and the total temperature of the image of the lateral view of the carcass of the animal after slaughter.

11. The process of claim 7, wherein said thermographic images comprise an image of the dorsal view of the live animal, an image of the lateral view of the live animal, and an image of the distal view of the live animal; and said statistical measures comprise the mean temperature of the image of the dorsal view of the live animal, the mean temperature of the image of the lateral view of the live animal, the mean temperature of the image of the distal view of the live animal, the standard deviation of temperature of the image of the dorsal view of the live animal, the standard deviation of temperature of the image of the lateral view of the live animal, and the standard deviation of temperature of the image of the distal view of the live animal.

12. The process of any one of claims 8, 9, 10, or 11, wherein said animal is of the species Bos taurus or Bos indicus.

13. The process of claim 12, wherein said tissue composition characteristic is lean body mass.

14. The process of claim 1, wherein said at least one thermographic image comprises an image of the dorsal view of the live animal, and said at least one statistical measure comprises the total temperature of the image of the dorsal view of the live animal.

15. The process of claim 14, wherein said animal is of the species Sus domesticus or Sus scrofa.

16. The process of claim 15, wherein said tissue composition characteristic is lean yield.

17. The process of claim 1, wherein said at least one thermographic image comprises an image of the dorsal view of the live animal and said at least one statistical measure comprises the mean temperature of the image of the dorsal view of the live animal.

18. The process of claim 17, wherein said animal is of the species Bos taurus or Bos indicus.

19. The process of claim 18, wherein said tissue composition characteristic is grade classification.

20. An apparatus for determining the value of a tissue composition characteristic of an animal, comprising:
    image acquisition means for obtaining either or both of at least one infrared thermographic image of said animal while it is alive, taken from at least one view, and at least one infrared thermographic image of the carcass of said animal after slaughter, taken from at least one view;

computing and storage means for:
  storing each of said obtained images as an array of pixels providing temperature data representative of temperature information at the corresponding part of the image;
  calculating the value of at least one statistical measure of the temperature data for each thermographic image;
  providing a predictive model wherein said tissue composition characteristic is included as an output variable, and said statistical measures of temperature data are included as input variables;
  solving said predictive model to provide the value of said tissue composition characteristic; and,
output means for providing an output of the value of said tissue composition characteristic.

21. The apparatus of claim 20, wherein said statistical measures are selected from the group consisting of a measure of central tendency, a measure of dispersion, and a total temperature.

22. The apparatus of claim 20, wherein said at least one infrared thermographic image includes at least one infrared thermographic image of said animal while it is alive, taken from at least one view.

23. The apparatus of claim 20, wherein said at least one infrared thermographic image includes at least one infrared thermographic image of the carcass of said animal after slaughter, taken from at least one view.

24. The apparatus of claim 20, wherein said tissue composition characteristic is selected from the group consisting of lean body mass, cuttability, degree of marbling, percent carcass yield, lean yield, rib eye area, loin eye area, subcutaneous fat thickness and grade classification.

25. The apparatus of claim 20, wherein said computing and storage means further comprises means for:
  storing the value of at least one property of said animal, obtained either before or after slaughter, that does not provide temperature information;
and wherein said property that does not provide temperature information is included as an input variable in said predictive model.

26. The apparatus of claim 25, wherein said property that does not provide temperature information is the live weight of said animal.

27. The apparatus of claim 26, wherein said thermographic images comprise an image of the distal view of the live animal; and said statistical measures comprise the mean temperature of the image of the distal view of the live animal and the standard deviation of temperature of the image of the distal view of the live animal.

28. The apparatus of claim 26, wherein said thermographic images comprise an image of the dorsal view of the live animal, an image of the lateral view of the live animal, and an image of the distal view of the live animal; and said statistical measures comprise the total temperature of the image of the dorsal view of the live animal, the total temperature of the image of the distal view of the live animal, the total temperature of the image of the lateral view of the live animal, the standard deviation of temperature of the image of the dorsal view of the live animal, the standard deviation of temperature of the image of the lateral view of the live animal, and the standard deviation of temperature of the image of the distal view of the live animal.

29. The apparatus of claim 28, wherein said thermographic images further comprise an image of the lateral view of the carcass of the animal after slaughter; and said statistical measures further comprise the standard deviation of temperature of the image of the lateral view of the carcass of the animal after slaughter, and the total temperature of the image of the lateral view of the carcass of the animal after slaughter.

30. The apparatus of claim 26, wherein said thermographic images comprise an image of the dorsal view of the live animal, an image of the lateral view of the live animal, and an image of the distal view of the live animal; and said statistical measures comprise the mean temperature of the image of the dorsal view of the live animal, the mean temperature of the image of the lateral view of the live animal, the mean temperature of the image of the distal view of the live animal, the standard deviation of temperature of the image of the dorsal view of the live animal, the standard deviation of temperature of the image of the lateral view of the live animal, and the standard deviation of temperature of the image of the distal view of the live animal.

31. The apparatus of any one of claims 27, 28, 29, or 30, wherein said animal is of the species Bos taurus or Bos indicus.

32. The apparatus of claim 31, wherein said tissue composition characteristic is lean body mass.

33. The apparatus of claim 20, wherein said at least one thermographic image comprises an image of the dorsal view of the live animal, and said at least one statistical measure comprises the total temperature of the image of the dorsal view of the live animal.

34. The apparatus of claim 33, wherein said animal is of the species Sus domesticus or Sus scrofa.

35. The apparatus of claim 34, wherein said tissue composition characteristic is lean yield.

36. The apparatus of claim 20, wherein said at least one thermographic image comprises an image of the dorsal view of the live animal, and said at least one statistical measure comprises the mean temperature of the image of the dorsal view of the live animal.

37. The apparatus of claim 36, wherein said animal is of the species Bos taurus or Bos indicus.

38. The apparatus of claim 37, wherein said tissue composition characteristic is grade classification.

* * * * *